United States Patent [19]

Nayak

[11] Patent Number: 5,085,865
[45] Date of Patent: Feb. 4, 1992

[54] SUSTAINED RELEASE PHARMACEUTICAL PREPARATIONS CONTAINING AN ANALGESIC AND A DECONGESTANT

[75] Inventor: Ammunje S. Nayak, Great Meadows, N.J.

[73] Assignee: Warner-Lambert Company, Morris Plains, N.J.

[21] Appl. No.: 336,929

[22] Filed: Apr. 12, 1989

[51] Int. Cl.[5] .......................... A61K 9/22; A61K 9/24
[52] U.S. Cl. .................... 424/472; 424/465; 424/468; 424/469; 424/470; 424/480; 514/853
[58] Field of Search ............... 424/468, 469, 470, 472, 424/473, 480

[56] References Cited

U.S. PATENT DOCUMENTS

| | | | |
|---|---|---|---|
| 3,567,819 | 3/1971 | Idson et al. | 424/16 |
| 4,189,469 | 2/1980 | Gleixner et al. | 424/78 |
| 4,226,848 | 10/1980 | Nagai et al. | 424/19 |
| 4,250,163 | 2/1981 | Nagai et al. | 424/14 |
| 4,260,596 | 4/1981 | Mackles | 424/14 |
| 4,427,681 | 1/1984 | Munshi | 424/260 |
| 4,449,983 | 5/1984 | Cortese et al. | 604/892 |
| 4,601,894 | 7/1986 | Hanna et al. | 424/19 |
| 4,657,757 | 4/1987 | Hanna et al. | 424/488 |
| 4,678,516 | 7/1987 | Alderman et al. | 106/197.1 |
| 4,695,591 | 9/1987 | Hanna et al. | 514/781 |
| 4,777,050 | 10/1988 | Vadino | 424/468 |
| 4,789,549 | 12/1988 | Khan et al. | 424/480 |
| 4,820,522 | 4/1989 | Radebaugh et al. | 424/468 |
| 4,820,523 | 4/1989 | Shtohryn et al. | 424/468 |
| 4,844,907 | 7/1989 | Elger et al. | 424/472 |
| 4,851,233 | 7/1989 | Khan et al. | 424/468 |

FOREIGN PATENT DOCUMENTS

| | | |
|---|---|---|
| 0111144 A | 6/1984 | European Pat. Off. . |
| 8808299 | 11/1988 | PCT Int'l Appl. . |
| 874580 | 8/1961 | United Kingdom . |
| 1334732 | 10/1973 | United Kingdom . |
| 1551698 | 8/1979 | United Kingdom . |
| 2123291 | 2/1984 | United Kingdom . |

OTHER PUBLICATIONS

The Theory and Practice of Industrial Pharmacy, 2nd Ed., Lea & Febiger, Phil. U.S.A., 1976, pp. 343, 344.
*Formulating For Controlled Release with METHOCEL Cellulose Ethers,* Form No. 192-1029-387, The Dow Chemical Company, Dow Chemical U.S.A., Specialty Chemical Department (1987).

Primary Examiner—Thurman K. Page
Assistant Examiner—James M. Spear
Attorney, Agent, or Firm—Sandra Gusciorafield; Charles A. Gaglia, Jr.

[57] ABSTRACT

An orally administrable sustained-release pharmaceutical tablet having at least two layers, which are directly compressible, is disclosed. The first layer, an immediate-release layer, contains an orally active analgesic and is readily susceptible to disintegration in the stomach. The second layer, a sustained-release layer which is directly compressed onto the first layer, comprises an orally active decongestant admixed with a major amount of a sustained-release agent so as to display increased resistance to disintegration and erosion in the gastro-intestinal tract relative to the first layer.

7 Claims, No Drawings

SUSTAINED RELEASE PHARMACEUTICAL PREPARATIONS CONTAINING AN ANALGESIC AND A DECONGESTANT

The present invention relates to an orally administrable combined immediate-release/sustained-release directly compressible pharmaceutical tablet for symptomatic relief of sinus headache and post nasal drip. The inventive tablet contains at least two layers which comprise an analgesic composition layer for immediate-release and a decongestant composition layer for sustained-release over a 12 hour period.

BACKGROUND OF THE INVENTION

The preparation of immediate-release and sustained-release dosage forms is well known. One major problem has been the preparation of a single dosage form wherein one medicament is to be provided for immediate-release and another medicament, or more of the same medicament, is provided for sustained-release over a longer, specific period of time.

U.S. Pat. Nos. 4,226,848 and 4,250,163 to Nagai et al. disclose a method for the controlled administration a medicament to the mucosa of the nasal cavity or the oral cavity by adhering the medicament with a polymeric matrix comprising about 50% to about 95% cellulose ether, such as methyl cellulose, hydroxypropylmethyl cellulose and the like, and about 50% to about 5% homopolymer or copolymer of acrylic acid. The medicament may be analgesic and anti-inflammatory agents, antihistamines, antibiotics, antibacterial agents, chemotherapeutic agents, local anesthesics, cardiac agents, vasodilators, antitussives and expectorants, oral antiseptics, enzyme proteins, hypoglycemic agents, hemostats, hormones, hypotensive agents, sedatives or tranquilizers, antitumor agents, gastro-intestinal drugs and antacids. The medicament is uniformly dispersed into the polymeric matrix and formed, by conventional means, into tablets, granules, powders and the like. The adherence of the preparation to the particular muscosal area allows a high concentration of medicament to be applied locally to a diseased area or to an optimal site of absorption.

European Patent No. A-0111144 to Merrell Dow Pharmaceuticals, Inc. teaches a sustained-release, solid dosage form having a core and one or more concentric enveloping sustained-release layers wherein the concentration of the medicament is greatest in the core and diminishes in each subsequent outer layer which allows zero-order release of the medicament. This disclosure provides further teaching in that the outer layer is a quickly-dissolving nonsustained-release layer which allows rapid onset of medicament effect and the underlying layers provide sustained-release medicaments, as does the core. The matrix is a hydrophilic gel such as hydroxypropyl methylcellulose or mixtures of such gels to effect particular release rates.

U.S. Pat. No. 4,260,596 to Mackles describes an edible unit dosage form having a hard outer shell comprising about 80% to about 100% mannitol which encloses a soft or liquid inner medicament-containing center. The outer shell is sealed by use of a sealing mixture which is poured into an opening in the shell, then allowed to cool and harden. Typical medicaments include topical antiseptics, topical anesthetics, analgesics and antipyretics, cough suppressants, antihistamines, pulmonary decongestants, antacids and the like and mixtures thereof.

U.S. Pat. No. 4,427,681 to Munski teaches a thixotropic gel composition containing a mixture of microcrystalline cellulose, sodium carboxymethylcellulose as the suspending agent and titanium dioxide as an opacifying agent which is easily convertible by moderate hand shaking into a pourable liquid. Typical compositions include cough syrups and sore throat and cough suppressant medication formulations. Typical medicaments may include combinations of pseudoephedrine and salicylates.

U.S. Pat. No. 4,449,983 to Cortese et al. describes an osmotic device in which the medicament compartments are separated by a hydrogel (swellable, hydrophilic polymer) such as cross-linked poly(hydroxyalkyl methacrylate) and poly(-vinyl alcohol) material. The outer wall of the device is formed from osmosis and reverse osmosis polymers such as cellulose acylate, cellulose acetate, beta-glycan acetate, polyurethane, cellulose acetate succinate, and the like. Medicament combinations can include decongestants and analgesics.

U.S. Pat. Nos. 4,601,894 and 4,657,757 to Hanna et al. disclose controlled-release matrix dosage forms containing acetaminophen, pseudoephedrine sulfate and dextrobrompheniramine maleate in a single homogeneous mixture of hydroxypropyl methylcellulose and ethers and other cellulose and cellulose ether derivatives which provide release of each active at its desired rate over a period of 2-14 hours.

U.S. Pat. No. 4,678,516 to Alderman et al. teaches a thermoformable sustained-release matrix comprised of hydroxypropyl methylcellulose and a major amount (at least about 30% by weight) of a plasticizer such as polyethylene glycol. Typical medicaments include herbicides, insecticides, nematocides, fungicides, antimicrobials, medicaments, vitamins, coloring agents and preservatives.

U.S. Pat. No. 4,695,591 to Hanna et al. is directed to a controlled-release dosage form incorporating an analgesic-effective amount of acetaminophen, an antihistaminic-effective amount of dexbrompheniramine maleate, a decongestant-effective amount of pseudoephedrine sulfate and 4.6% to 12% hydroxypropyl methycellulose U.S.P. 2910 as the carrier base. This dosage form is prepared by (1) blending all of the ingredients together, (2) granulating the powder blend, (3) drying the granules and milling if necessary, (4) blending the granules with lubricants, and (5) compressing and then coating the compressed tablets, if desired.

U.S. Pat. No. 4,789,549 to Khan et al. discloses a sustained-release dosage form wherein the tendency for an initial surge of medicament in the first hour is prevented, comprising coating a medicament in a water soluble polymer matrix with a semipermeable membrane consisting of hydroxypropyl cellulose and cellulose acetate phthalate with polyoxpropylene polyoxethylene block copolymer and acetylated monoglycerides. The ratio of medicament to water soluble polymer matrix can vary from about 90%:10% to about 78%:22%. The preferred medicament is diphenhydramine hydrochloride or disopyramide phosphate.

Applicant has unexpectedly found a solution to the two medicament delivery system problem by providing a tablet comprising at least two layers wherein the first layer is readily disintegratable and provides immediate-release of the medicament and the second layer displays increased resistance to disintegration and erosion relative to the first layer and thereby provides sustained-release of the medicament. Applicant's inventive tablet also provides the advantage of being a directly compressible layered tablet.

DETAILED DESCRIPTION OF THE INVENTION

The present invention sets forth a directly compressible pharmaceutical composition having at least two compressed layers intimately bonded to each other, a first layer which is readily susceptible to disintegration in the stomach and a second layer which displays increased resistance to disintegration and erosion in the gastro-intestinal tract relative to the first layer. Upon administration, the first layer, being a nonsustained-release matrix, releases its medicament immediately while the second layer, being a sustained-release matrix and more slowly disintegratable layer, releases its medicament over a longer period of time.

The first layer comprises an effective amount of an orally active analgesic corresponding to a single effective dose, which may be admixed with a minor amount of excipients, to form a pharmaceutically elegant layer which will provide immediate-release of the analgesic in the stomach. The orally active analgesic can be acetaminophen, acetylsalicylic acid, ibuprofen, and the like, preferably acetaminophen. Generally, excipients can include diluents, binders or adhesives, lubricants or antiadherents, disintegrants, colorants, sweeteners and adsorbents. A lubricant may be included in an amount of from about 0 to about 5% by weight of the analgesic composition layer. Suitable lubricants include magnesium stearate, calcium stearate, zinc stearate, colloidal silicon dioxide and stearic acid. Preferably, the lubricant for the analgesic composition layer is stearic acid in an amount of about 3% by weight of the analgesic composition layer. A binder, such as water soluble hydroxyalkyl cellulose, may be included in an amount of from about 0 to about 10% by weight of the analgesic composition layer. A disintegrant, such as sodium croscarmelose, sodium lauryl sulfate, starch or sodium starch glycolate, may be included in an amount of about 0 to about 10% by weight of the analgesic composition layer.

The second layer comprises an effective amount of an orally active decongestant corresponding to a dosage amount for controlled, sustained-release of effective amounts of the decongestant over a 12 hour time period admixed with a major amount of a sustained-release agent. The second layer is more resistant to disintegration and erosion in the gastro-intestinal tract relative to the first layer. Typically, the decongestant in the second layer is selected from the group consisting of pseudoephedrine, pseudoephedrine hydrochloride or pseudoephedrine sulfate. The amount of decongestant therein incorporated should be sufficient to release effective amounts thereof over a period of about 12 hours. Preferably, the decongestant is included in an amount of about 60 mg. per tablet One or more hydrogels are the preferred sustained-release agent. The ratio of the hydrogel to the decongestant in the second layer is from about 2:1 to about 7:1. Suitable hydrogels include water soluble hydroxyalkyl celluloses. Preferably, the hydrogels will be one or more of hydroxyethyl cellulose, hydroxypropyl cellulose, hydroxypropyl methylcellulose or mixtures thereof. Sodium croscarmelose or other similar disintegrating agent may also be included for its water absorbability or water swellability properties to assist in hydration of the hydrogel. Most preferably, the sustained-release agent is a mixture of hydroxypropyl cellulose and sodium croscarmelose. The amount of hydrogel incorporated as a sustained-release agent will be from about 25% to about 90% by weight of the decongestant composition layer. From about 25% to about 100% of the hydrogel can be hydroxypropyl cellulose alone or in combination with up to about 50% hydroxyethylcellulose or up to about 50% hydroxypropyl methylcellulose. Up to about 20% sodium croscarmelose may also be included in the sustained-release agent. The second layer may also contain one or more pharmaceutical excipients such as lubricants, fillers and/or disintegrants, i.e., magnesium stearate, calcium stearate, zinc stearate, colloidal silicon dioxide, stearic acid, polyethylene glycol, starch, sodium croscarmelose, povidone, sugar, carboxymethyl starch and microcrystalline cellulose. These additional ingredients can be included in the second layer in an amount from about 0 to about 50%.

The two layers are formulated independently and tablets are prepared from the two formulations using a two layer press. The first analgesic-containing layer is fed into the press and directly compressed to a hardness of about 2 to about 3 Kp, then the second decongestant-containing layer is fed into the press on top of the first layer and directly compressed thereupon to achieve a total final tablet hardness of about 8 to about 12 Kp.

The following examples are illustrative of the nature of the invention but should not be construed as a limitation thereof. The scope of the invention is defined solely in the appended claims. All percentages used herein are based by weight of the total dosage form unless otherwise indicated.

EXAMPLE 1

| Ingredient | Amount per 1000 Tablets |
| --- | --- |
| 1. Acetaminophen USP 90% | 550.0 g |
| 2. Croscarmelose Sodium NF | 5.5 g |
| 3. Stearic Acid USP | 16.5 g |
| 4. Pseudoephedrine HCl USP | 60.0 g |
| 5. Hydroxypropyl Cellulose | 360.0 g |
| 6. Polyvinylpyrolidone USP | 10.0 g |
| 7. Confectioners Sugar USP | 5.0 g |
| 8. Mag. Stearate NF | 3.0 g |
| 9. Purified Water USP | 400.0 ml |

Layer 1: Ingredients 2 and 3 were screened then admixed with ingredient 1 by blending in a suitable blender for a sufficient time to produce a uniform mixture.

Layer 2: Independently, ingredients 4, 5 and 7 were mixed and granulated in a suitable granulator mixer with a solution of ingredient 6 and part of ingredient 9. Additional water may be added as needed to prepare a satisfactory granulation. The granulation was dried at about 40° to about 45° C. for about 10 to about 12 hours, milled to a particle size range such that about 0 to about 20% is retained on a #20 mesh screen, U.S. Std. Sieve, about 0 to about 10% is retained on a #30 mesh screen, about 0 to about 15% is retained on a #60 mesh screen, about 0 to about 10% is retained on a #80 mesh screen, about 0 to about 30% is retained on a #100 mesh screen, and about 0 to about 50% remained in the pan. The milled granulation was then blended with ingredient 8.

Tablets were prepared using 2-layer press by first compressing layer 1 to a hardness of about 2 to about 3

Kp followed by directly compressing layer 2 immediately thereupon to prepare a two layer tablet having a total final tablet hardness of about 8 to about 12 Kp.

The following dissolution release pattern was observed using USP Dissolution Method 2:

|  | % Drug Dissolved | | | | |
| --- | --- | --- | --- | --- | --- |
| Time (hours) | 1 | 3 | 5 | 7 | 12 |
| Pseudoephredrine HCl | 45 | 67 | 80 | 90 | 100 |
| Acetaminophen | 95 | 100 | — | — | — |

EXAMPLE 2

| Ingredient | Amount per 1000 Tablets |
| --- | --- |
| 1. Acetaminophen USP 90% | 550.00 g |
| 2. Croscarmelose Sodium NF | 5.50 g |
| 3. Stearic Acid USP | 16.50 g |
| 4. Pseudoephedrine HCl USP | 60.00 g |
| 5. Hydroxyethyl Cellulose | 360.00 g |
| 6. Magnesium Stearate NF | 2.50 g |
| 7. Silicone Dioxide, Colloidal NF | 1.00 g |

Layer 1: Ingredients 2 and 3 were screened then admixed by blending with ingredient 1 in a suitable blender for sufficient time to produce a uniform mixture.

Layer 2: Independently, ingredients 4 and 5 were screened and blended, then ingredients 6 and 7 were screened and blended, then admixed with the mixture of ingredients 4 and 5 by blending in a suitable blender for sufficient time to produce a uniform mixture.

Tablets were prepared using a 2-layer press by first compressing layer 1 to a hardness of about 2 to about 3 Kp followed by directly compressing layer 2 immediately thereupon to prepare a two layer tablet having a total final tablet hardness of about 8 to about 12 Kp.

The following dissolution release pattern was observed using USP Dissolution Method 2:

|  | % Drug Dissolved | | | | |
| --- | --- | --- | --- | --- | --- |
| Time (hours) | 1 | 3 | 5 | 7 | 12 |
| Pseudoephredrine HCl | 44 | 74 | 89 | 90 | 100 |
| Acetaminophen | 77 | 95 | 100 | — | — |

EXAMPLE 3

| Ingredient | Amount per 1000 Tablets |
| --- | --- |
| 1. Acetaminophen USP 90% | 550.00 g |
| 2. Croscarmelose Sodium NF | 5.50 g |
| 3. Stearic Acid USP | 16.50 g |
| 4. Pseudoephedrine HCl USP | 60.00 g |
| 5. Hydroxyethyl Cellulose | 360.00 g |
| 6. Croscarmelose Sodium NF | 34.00 g |
| 7. Magnesium Stearate NF | 2.50 g |
| 8. Silicone Dioxide, Colloidal NF | 1.00 g |

Layer 1: Ingredients 2 and 3 were screened and admixed with ingredient 1 by blending in a suitable blender for sufficient time to produce a uniform mixture.

Layer 2: Independently, ingredients 4 and 5 were screened and blended, then ingredients 6, 7 and 8 were screened and blended, then admixed with ingredients 4 and 5 by blending in a suitable blender for sufficient time to produce a uniform mixture.

Tablets were prepared using 2-layer press by first compressing layer 1 to a hardness of about 2 to about 3 Kp followed by directly compressing layer 2 immediately thereupon to prepare a two layer tablet having a total final tablet hardness of about 8 to about 12 Kp.

The following dissolution release pattern was observed using USP Dissolution 2:

|  | % Drug Dissolved | | | | |
| --- | --- | --- | --- | --- | --- |
| Time (hours) | 1 | 3 | 5 | 7 | 12 |
| Pseudoephredrine HCl | 36 | 60 | 70 | 80 | 88 |
| Acetaminophen | 95 | 100 | — | — | — |

EXAMPLE 4

Bioavailability studies were conducted on four volunteers each of whom received a single dose of two tablets as prepared above in Example 1, 2 and 3. A direct comparison using Sudafed ® SA capsules was also conducted (Sudafed is a trademark of the Burroughs Wellcome Co. of Research Triangle Park, N.C.). Blood samples were withdrawn at 1, 2, 3, 4, 6, 7, 8, 12, 18, and 24 hours and assayed for pseudoephedrine. The following results were obtained:

| TIME hours | PSEUDOEPHEDRINE (ng/ml) - MEAN VALUE | | | |
| --- | --- | --- | --- | --- |
|  | Example 1 | Example 2 | Example 3 | Sudafed SA capsule |
| 1 | 97.25 ± 16.06 | 148.60 ± 60.65 | 128.50 ± 15.98 | 123.68 ± 37.48 |
| 2 | 164.90 ± 15.55 | 273.65 ± 132.98 | 203.90 ± 26.56 | 195.80 ± 52.16 |
| 3 | 191.90 ± 18.98 | 270.78 ± 33.44 | 231.30 ± 16.78 | 230.15 ± 63.57 |
| 4 | 221.18 ± 28.28 | 314.83 ± 13.16 | 258.20 ± 25.24 | 247.20 ± 75.58 |
| 6 | 233.53 ± 25.05 | 325.45 ± 24.79 | 299.38 ± 14.37 | 238.65 ± 65.23 |
| 7 | 240.08 ± 30.04 | 328.70 ± 33.51 | 292.45 ± 14.52 | 251.78 ± 52.33 |
| 8 | 228.50 ± 39.20 | 308.35 ± 29.30 | 226.50 ± 11.40 | 247.58 ± 47.59 |
| 12 | 216.95 ± 59.97 | 231.23 ± 35.95 | 226.50 ± 11.40 | 174.65 ± 30.90 |
| 18 | 146.80 ± 52.36 | 127.68 ± 42.70 | 133.75 ± 27.19 | 96.90 ± 27.28 |
| 24 | 83.48 ± 42.24 | 64.08 ± 26.47 | 68.95 ± 27.81 | 48.13 ± 17.92 |

These studies show that the sustained-release of pseudoephedrine from the inventive two layer tablets is comparable to the sustained-release from Sudafed ® SA capsules.

The invention as thus thereinbefore described may obviously be varied in many ways. Such variations are not to be regarded as a departure from the spirit and scope of the invention and all such modifications are intended to be included within the scope of the following claims.

What is claimed is:

1. An orally administrable pharmaceutical tablet having at least two layers, comprising a first and a second layer directly compression bonded to each other,
   (a) wherein said first layer is readily susceptible to disintegration in the stomach and comprises an effective amount, for immediate-release, of an orally active analgesic, and
   (b) wherein said second layer displays increased resistance to disintegration and erosion in the gastrointestinal tract relative to said first layer and comprises an effective amount, for sustained-release over a 12 hour time period, of an orally active decongestant admixed with from about 25% to about 90% by weight of the decongestant composition layer of a sustained-release agent comprising one or more hydrogels selected from the group consisting of water soluble hydroxyalkylcelluloses wherein said orally active decongestant is selected from the group consisting of pseudoephedrine, pseudoephedrine hydrochloride and pseudoephedrine sulfate.

2. An orally administrable pharmaceutical tablet according to claim 1 wherein the orally active analgesic is acetaminophen.

3. An orally administrable pharmaceutical tablet comprising a first and second layer directly compression bonded to each other, said first layer being readily susceptible to disintegration in the stomach and comprising an effective amount of acetaminophen, and said second layer displaying increased resistance to disintegration and erosion in the gastro-intestinal tract relative to said first layer and comprising a quantity of pseudoephedrine, pseudoephedrine hydrochloride or pseudoephedrine sulfate admixed with from about 25% to about 90% by weight of the decongestant composition layer of a hydrogel selected from the group consisting of water soluble hydroxyalkylcelluloses and a minor amount of sodium croscarmelose, wherein the ratio of said hydrogel to pseudoephedrine in said second layer is from about 2:1 to about 7:1 and the amount of pseudoephedrine, pseudoephedrine hydrochloride or pseudoephedrine sulfate in said second layer is at least sufficient to release amounts thereof which are effective as a decongestant over a period of about twelve hours.

4. An orally administrable pharmaceutical tablet according to claim 1 wherein said hydrogels are selected from the group consisting of hydroxyethyl cellulose, hydroxypropyl cellulose, hydroxypropyl methylcellulose, and mixtures thereof.

5. An orally administrable pharmaceutical tablet according to claim 1 wherein the ratio of said hydrogel to said decongestant in said second layer is from about 2:1 to about 7:1.

6. An orally administrable pharmaceutical tablet according to claim 1 which further includes in said second layer a minor amount of one or more disintegrants.

7. An orally administrable pharmaceutical tablet according to claim 6 wherein the disintegrant is sodium croscarmelose.

* * * * *